United States Patent [19]

King

[11] Patent Number: 5,262,534
[45] Date of Patent: Nov. 16, 1993

[54] PROCESS FOR THE PREPARATION OF NONAROMATIC CYCLIC NITROGEN-CONTAINING COMPOUNDS

[75] Inventor: Stephen W. King, Scott Depot, W. Va.

[73] Assignee: Union Carbide Chemicals & Plastics Technology Corporation, Danbury, Conn.

[21] Appl. No.: 892,641

[22] Filed: Jun. 2, 1992

Related U.S. Application Data

[63] Continuation of Ser. No. 585,560, Sep. 20, 1990, abandoned.

[51] Int. Cl.⁵ ............... C07D 295/03; C07D 295/023
[52] U.S. Cl. ................... 544/162; 544/178; 544/402; 544/410
[58] Field of Search ............ 544/410, 178, 162; 560/24

[56] References Cited

U.S. PATENT DOCUMENTS 2,356,764  8/1944  Kern ........................... 564/24
2,973,362  2/1961  Schorsch ........................ 260/268

FOREIGN PATENT DOCUMENTS 1670240  3/1972  Fed. Rep. of Germany .

OTHER PUBLICATIONS

March, Advanced Organic Chemistry, (1968), pp. 435–436, 477–480, 878–879.
Enichem Synthesis SpA, Dimethyl Carbonate Product Bulletin, pp. 10–13 (date not available).
Dow Chemical U.S.A., Experimental Ethylene Carbonate XAS-1666.001 Product Bulletin (1982), pp. 5–7.
Trotta, et al.; J. Org. Chem., 1987, 52, pp. 1300–1304.
Texaco Chem. Co., Texacar ®-Ethylene & Propylene Carbonates Product Bulletin (1987), pp. 22–23.

Primary Examiner—Joseph Paul Brust
Attorney, Agent, or Firm—R. M. Allen

[57] ABSTRACT

A process for preparing nonaromatic N,N,N-trisubstituted nitrogen-containing compounds which comprises heating a nonaromatic carboxylated N,N,N-trisubstituted nitrogen-containing compound at an elevated temperature for a period of time sufficient to produce the nonaromatic N,N,N-trisubstituted nitrogen-containing compound.

7 Claims, No Drawings

PROCESS FOR THE PREPARATION OF NONAROMATIC CYCLIC NITROGEN-CONTAINING COMPOUNDS

This application is a continuation of Ser. No. 07/585,560, filed Sep. 20, 1990, now abandoned.

RELATED APPLICATIONS

The following are related, commonly assigned applications, filed on an even data herewith:

U.S. Pat. application Ser. No. 07/585,561; U.S. Pat. application Ser. No. 07/585,455 now U.S. Pat. No. 5,210,322; U.S. Pat. application Ser. No. 07/585,563 now U.S. Pat. No. 5,214,142; U.S. Pat. application Ser. No. 07/585,564 U.S. Pat. application Ser. No. 07/585,559 now U.S. Pat. No. 5,191,123, U.S. Pat. application Ser. No. 07,585,456 now U.S. Pat. No. 5,220,069; U.S. Pat. application Ser. No. 07/585,458 now U.S. Pat. No. 5,112,984; U.S. Pat. application Ser. No. 07/585,565 now U.S. Pat. No. 5,194,613; U.S. Pat. application Ser. No. 07/585,555 now U.S. Pat. No. 5,104,987; U.S. Pat. application Ser. No. 07/585,556 now U.S. Pat. No. 5,164,497 and U.S. Pat now U.S. Pat. No. 5,116,531 all of which are incorporated herein by reference.

BRIEF SUMMARY OF THE INVENTION

Technical Field

This invention relates to a process for preparing nonaromatic N,N,N-trisubstituted nitrogen-containing compounds which comprises heating a nonaromatic carboxylated N,N,N-trisubstituted nitrogen-containing compound at an elevated temperature for a period of time sufficient to produce the nonaromatic N,N,N-trisubstituted nitrogen-containing compound.

BACKGROUND OF THE INVENTION

Decarboxylation, that is, elimination of the —COOH group as $CO_2$, is a known process. March, J., Advanced Organic Chemistry: Reactions, Mechanisms, and Structure, 1968, pp. 453–436, 477–480 and 878–879, describes various decarboxylation reactions. At pages 435–436, it is stated that aromatic acids can be decarboxylated by heating with copper and quinoline. At pages 477–480, it is stated that aliphatic acids which undergo successful decarboxylation have certain functional groups or double or triple bonds in the alpha or beta positions such as malonic acids, alpha-cyano acids, alpha-nitro acids, alpha-aryl acids, alpha-keto acids, alpha-trihalo acids, beta-keto acids, beta,gamma-olefinic acids and the like. At pages 878–879, oxidative decarboxylation is described in which lead tetraacetate cleaves carboxyl groups, replacing them with acetoxy groups, which may be hydrolyzed to hydroxyl groups. It is stated that compounds containing carboxyl groups on adjacent carbons (succinic acid derivatives) can be bisdecarboxylated with lead tetraacetate. It is also stated that compounds containing geminal carboxyl groups (malonic acid derivatives) can be biscarboxylated with lead tetraacetate, gem-diacetates (acylals) being produced, which are hydrolyzable to ketones.

Enichem Synthesis SpA, Dimethyl Carbonate Product Bulletin, pp. 10–13, discloses the reaction of aromatic amines with dimethyl carbonate to give N-methyl and N,N′-dimethyl aromatic amines. It is stated that the reaction is carried out under the same conditions as used for the methylation of phenols. The reaction of phenols with dimethyl carbonate is carried out in the presence of a basic catalyst such as NaOH, $Na_2CO_3$, $NaOCH_3$, tertiary amines and heterocyclic nitrogenous compounds. Reaction temperatures of at least 140° C. are required. It is stated that the speed of reaction can be accelerated with catalytic quantities of organic and inorganic halides. At page 12, it is stated that dimethyl carbonate reacts with amines (aliphatic or aromatic, primary or secondary) to Produce carbamates and ureas. At page 13, it is stated that aminoalcohols can react with dimethyl carbonate in the presence of sodium or potassium alkoxides to yield 2-oxazolidinones.

Dow Chemical U.S.A., Experimental Ethylene Carbonate XAS-1666.00L Product Bulletin (1982), pp. 5–7, discloses that aromatic amines can be reacted with ethylene carbonate to form N-(2-hydroxyethyl) derivatives. It is stated that with primary amines such as aniline, a mixture of mono- and di-substituted derivatives can be prepared. It is also stated that carbamates and imidazolidinones can be produced through the reaction of ethylene carbonate with aliphatic mono- and diamines.

Texaco Chemical Company, TEXACAR® Ethylene and Propylene Carbonates Product Bulletin (1987), pp. 22–23, describes the reaction of ethylene carbonate and propylene carbonate with primary and secondary aliphatic amines at low temperatures to yield carbamates. It is stated that ethylene carbonate and propylene carbonate can react with amines to give the corresponding hydroxyethyl and hydroxypropyl derivatives.

Trotta, F. et al., J. Org. Chem. 1987, 52, pp. 1300–1304, relates to selective mono-N-alkylation of aromatic amines by dialkyl carbonate under gas-liquid phase-transfer catalysis conditions (continuous flow process). The catalyst is a polyethylene glycol in the presence of a base ($K_2CO_3$).

DISCLOSURE OF THE INVENTION

This invention relates to a process for preparing nonaromatic N,N,N-trisubstituted nitrogen-containing compounds which comprises heating a nonaromatic carboxylated N,N,N-trisubstituted nitrogen-containing compound at an elevated temperature for a period of time sufficient to produce the nonaromatic N,N,N-trisubstituted nitrogen-containing compound.

This invention also relates to a process for preparing nonaromatic N,N,N-trisubstituted nitrogen-containing compounds which comprises contacting a nonaromatic N,N-disubstituted nitrogen-containing compound with a $CO_2$ synthon at an elevated temperature for a period of time sufficient to produce the nonaromatic N,N,N-trisubstituted nitrogen-containing compound.

This invention further relates to a process for preparing nonaromatic N,N,N-trisubstituted nitrogen-containing compounds which comprises (i) contacting a nonaromatic N,N-disubstituted nitrogen-containing compound with a $CO_2$ synthon under conditions effective to produce a nonaromatic carboxylated N,N,N-trisubstituted nitrogen-containing compound, and (ii) heating the nonaromatic carboxylated N,N,N-trisubstituted nitrogen-containing compound at an elevated temperature for a period of time sufficient to produce the nonaromatic N,N,N-trisubstituted nitrogen-containing compound.

The nonaromatic N,N,N-trisubstituted nitrogen-containing compounds produced in accordance with the processes of this invention are useful for a wide variety of applications such as solvents, liquid absorbents, polyurethane catalysts and the like. Preferred nonaromatic N,N,N-trisubtituted nitrogen-containing compounds produced by the processes of this invention include nonaromatic cyclic nitrogen-containing compounds having a ring tertiary-substituted nitrogen such as N- and N,N'-substituted piperazines and N-substituted morpholines.

For purposes of this invention, the term "$CO_2$ synthon" embraces $SO_2$ synthons such as sulfurous acids and sulfurous acid esters.

DETAILED DESCRIPTION

As indicated above, this invention relates to a process for preparing nonaromatic N,N,N-trisubstituted nitrogen-containing compounds which comprises heating a nonaromatic carboxylated N,N,N-trisubstituted nitrogen-containing compound at an elevated temperature for a period of time sufficient to produce the nonaromatic N,N,N-trisubstituted nitrogen-containing compound.

As also indicated above, this invention relates to a process for preparing nonaromatic N,N,N-trisubstituted nitrogen-containing compounds which comprises contacting a nonaromatic N,N-disubstituted nitrogen-containing compound with a $CO_2$ synthon at an elevated temperature for a period of time sufficient to produce the nonaromatic N,N,N-trisubstituted nitrogen-containing compound.

As further indicated above, this invention relates to a process for preparing nonaromatic N,N,N-trisubstituted nitrogen-containing compounds which comprises (i) contacting a nonaromatic N,N-disubstituted nitrogen-containing compound with a $CO_2$ synthon under conditions effective to produce a nonaromatic carboxylated N,N,N-trisubstituted nitrogen-containing compound, and (ii) heating the nonaromatic carboxylated N,N,N-trisubstituted nitrogen-containing compound at an elevated temperature for a period of time sufficient to produce the nonaromatic N,N,N-trisubstituted nitrogen-containing compound.

When a nonaromatic N,N-disubstituted nitrogen-containing compound and $CO_2$ synthon are employed as starting materials, it is believed that either a transesterification reaction followed by a decarboxylation reaction occurs or a nucleophilic attack at the alpha-carbon of the $CO_2$ synthon with concurrent elimination of an organic moiety occurs to provide the desired nonaromatic N,N,N-trisubstituted nitrogen-containing compound product. Further, a partial transesterification may occur to provide an activated intermediate which is more susceptible to nucleophilic attack by the nonaromatic N,N-disubstituted nitrogen-containing compound. The exact reaction mechanism is not fully appreciated but what is appreciated is that a nonaromatic N,N-disubstituted nitrogen-containing compound starting material and $CO_2$ synthon starting material can be contacted under conditions described herein to provide a nonaromatic N,N,N-trisubstituted nitrogen-containing compound product. It is also appreciated that a nonaromatic carboxylated N,N,N-trisubstituted nitrogen-containing compound can be heated at an elevated temperature for a period of time sufficient to provide a nonaromatic N,N,N-trisubstituted nitrogen-containing compound product.

Step (i) of certain processes of this invention can in general be referred to as a transesterification reaction. Any suitable transesterification catalyst can be employed in step (i). Such transesterification catalysts are known and include, for example, basic metal oxides, alkoxides and other basic metal salts such as potassium carbonate, sodium titanate and the like. Other suitable transesterification catalysts include, for example, Bronsted acids such as sulfuric acid and Lewis acids such as aluminum triisopropoxide. The transesterification catalyst employed in this invention may also contain support(s), binding agent(s) or other additives to stabilize or otherwise help in the manufacture of the catalyst. Both homogeneous and heterogeneous catalysts can be employed in the step (i) reaction. The amount of transesterification catalyst used in step (i) is dependent on the particular catalyst employed and can range from about 0.01 weight percent or less to about 10 weight percent or greater of the total weight of the starting materials.

Suitable nonaromatic N,N-disubstituted nitrogen-containing compound starting materials which can be employed in the step (i) transesterification reaction include any permissible nonaromatic N,N-disubstituted nitrogen-containing compound(s) such as those embraced by the formula RNHR wherein R is the same or different and is the residue of an organic compound. It is understood that the R substituents together can complete a heterocycloalkyl ring which can be substituted or unsubstituted. Preferred nonaromatic N,N-disubstituted nitrogen-containing compound starting materials include nonaromatic N,N-disubstituted acyclic and cyclic compounds such as diethanolamine, piperazine and morpholine. Illustrative nonaromatic N,N-disubstituted nitrogen-containing compound starting materials useful in this invention include, for example, diethanolamine, piperazine, 1-hydroxyethylpiperazine, 1-aminoethylpiperazine, 1-methylpiperazine, 1-ethylpiperazine, morpholine and the like. The molar ratio of nonaromatic N,N-disubstituted nitrogen-containing compound to $CO_2$ synthon is not narrowly critical and can range from about 0.05:1 or less to about 50:1 or greater, preferably from about 0.1:1 to about 10:1.

Suitable $CO_2$ synthon starting materials which can be employed in the step (i) transesterification reaction include any permissible substituted or unsubstituted carboxyl-containing compound(s) or carbonyl-containing compound(s) which are capable of reacting with a nonaromatic N,N-disubstituted nitrogen-containing compound under the process conditions described herein, such as those embraced by the formulae $R_1C(O)R_2$ or $R_1S(O)R_2$ wherein $R_1$ is hydrogen, halogen, amino, hydroxyl or the residue of an organic compound, and $R_2$ is amino, hydroxyl or the residue of an organic compound. Illustrative $CO_2$ synthons include, for example, substituted and unsubstituted carbonates, chlorocarbonates, carbonic acids, carbamates, carbamic acids, oxalates, 2-oxazolidinones, ureas, esters, phosgene, chloroformates, carbon dioxide, orthocarboxylates, sulfurous acids, sulfurous acid esters and the like. For purposes of this invention, carbon monoxide is also considered a $CO_2$ synthon for appropriate oxidative carbonylation reactions. Preferred $CO_2$ synthons include, for example, diethyl carbonate, ethylene carbonate, propylene carbonate, dimethyl carbonate, 2-oxazolidinone, urea, ethylene sulfite, N-(2-hydroxyethyl) 2-oxazolidinone, N-(2-aminoethyl) 2-oxazolidinone and the like. The use of $CO_2$ synthons prepared in situ such as the reaction of ethylene carbonate and monoethanolamine to give 2-oxazolidinone is encompassed within the scope of this invention.

As indicated above, $R_1$ and $R_2$ can be the residue of an organic compound. Illustrative residues of organic compounds include, for example, alkyl, aryl, alkylamino, arylamino, cycloalkyl, heterocycloalkyl, alkyloxy, aryloxy, cycloalkyloxy, heterocycloalkyloxy, alkyloxycarbonyl, aryloxycarbonyl, cycloalkyloxycarbonyl, heterocycloalkyloxycarbonyl, hydroxycarbonyl and the like. Additionally, for purposes of defining the $CO_2$ synthon by the formulae above, the $R_1$ and $R_2$ substituents together can complete a cycloalkyl ring or a heterocycloalkyl ring which can be substituted or unsubstituted. The $R_1C(O)R_2$ formula is also contemplated to embrace carbon dioxide and carbon monoxide.

The step (i) transesterification reaction can be conducted over a wide range of pressures ranging from atmospheric or subatmospheric pressures to superatmospheric pressures. However, the use of very high pressures has not been observed to confer any significant advantages but increases equipment costs. Further, it is preferable to conduct the step (i) reaction at reduced pressures of from about 1 mm Hg to less than about 760 mm Hg. The step (i) transesterification reaction is preferably effected in the liquid or vapor states or mixtures thereof.

The temperature of the step (i) transesterification reaction may be as low as about ambient temperature to about 300° C. Preferably, the reaction temperature ranges from about 50° C. to about 200° C., and most preferably from about 60° C. to about 120° C.

Suitable nonaromatic carboxylated N,N,N-trisubstituted nitrogen-containing compounds prepared by the step (i) transesterification reaction include any permissible nonaromatic carboxylated N,N,N-trisubstituted nitrogen-containing compounds which are capable of eliminating carbon dioxide under the process conditions described herein, such as those embraced by the formulae $RN(C(O)OR_1)R$ or $RN(C(O)OR_2)R$ wherein R, $R_1$ and $R_2$ are as defined above. It is understood that the R substituents together can complete a heterocycloalkyl ring which can be substituted or unsubstituted. Illustrative nonaromatic carboxylated N,N,N-trisubstituted nitrogen-containing compounds include, for example, methyl 1-piperazine carboxylate, ethyl 1-piperazine carboxylate, methyl 4-methyl-1-piperazine carboxylate, ethyl 4-ethyl-1-piperazine carboxylate, 2-oxazolidinone, N-(2-hydroxyethyl) 2-oxazolidinone, N-(2-aminoethyl) 2-oxazolidinone, methyl 1-morpholine carboxylate, ethyl 1-morpholine carboxylate and the like.

The nonaromatic carboxylated N,N,N-trisubstituted nitrogen-containing compounds prepared by the step (i) transesterification reaction may undergo one or more transesterifications prior to the step (ii) decarboxylation reaction. For example, a hydroxyl-containing compound may be reacted with the originally prepared nonaromatic carboxylated N,N,N-trisubstituted nitrogen-containing compound under conditions effective to prepare a different nonaromatic carboxylated N,N,N-trisubstituted nitrogen-containing compound. Suitable hydroxyl-containing compounds include those embraced by the formula $R_3OH$ wherein $R_3$ is the residue of an organic compound. This invention is not intended to be limited in any manner by the step (i) transesterification reaction.

The step (ii) decarboxylation reaction may be effected in the liquid or vapor or supercritical liquid states or mixtures thereof. In this context, the vapor phase reaction is intended to refer to the general vapor state of the starting materials. Though the step (ii) decarboxylation reaction conditions may range from subatmospheric or atmospheric to superatmospheric conditions, it is desirable to run the step (ii) reaction from about 1 mm Hg to about 5,000 mm Hg, preferably from about 100 mm Hg to about 2,500 mm Hg.

The temperature of the step (ii) decarboxylation reaction may be as low as about 50° C. to about 300° C. Preferably, the reaction temperature ranges from about 75° C. to about 250° C., and most preferably from about 100° C. to about 225° C.

Suitable nonaromatic carboxylated N,N,N-trisubstituted nitrogen-containing compounds for use in the step (ii) decarboxylation reaction can be prepared by the step (i) transesterification reaction or by other methods such as the carbonylation of nonaromatic N,N,N-trisubstituted nitrogen-containing compounds with carbon monoxide and oxygen at elevated temperatures in the presence of certain copper salts. Such a carbonylation process can be an alternative to the step (i) transesterification reaction and is encompassed within the generic scope of this invention. It is also appreciated that two or more $CO_2$ synthons can be reacted under conditions effective to produce a nonaromatic carboxylated N,N,N-trisubstituted nitrogen-containing compound.

The step (ii) decarboxylation reaction can be conducted in the presence of an inert diluent which can be either a liquid or gas. When a liquid diluent is employed, it should preferably be a good solvent for the starting materials, inert under the reaction conditions, and of such a nature that separation from the nonaromatic N,N,N-trisubstituted nitrogen-containing compound product will not be difficult. For instance, the boiling points of the diluent and the nonaromatic N,N,N-trisubstituted nitrogen-containing compound product should differ by an adequate amount and there should be no tendency of the diluent to form an azeotrope with the desired nonaromatic N,N,N-trisubstituted nitrogen-containing compound product.

Examples of useful liquid diluents that meet the foregoing qualifications include benzene, toluene, xylene, ethylbenzene, anisole, heptane, octane, nonane, decane, dibutyl ether, and the like. Hydrocarbons are preferred. Illustrative gaseous diluents include for example, nitrogen, methane, hydrogen, carbon monoxide or carbon dioxide. The gaseous diluent should of course be chosen so that it does not prevent the preparation of the desired products.

While the use of such diluents may be beneficial, the processes of this invention can be operated using pure starting material(s) as a liquid or gaseous feed. The degree of dilution of the starting materials with various diluents may vary considerably depending upon any process constraints restricting the use of the diluent. For example, in commercial production, the use of very large quantities of some gaseous diluents may be disadvantageous due to the cost of pumping large volumes of the gaseous diluent and increased difficulty in isolating the product, which increase the energy costs of the process. With liquid diluents, the use of very large quantities may be disadvantageous due to the energy cost associated with large recovery and recycle. If the processes of this invention are to be carried out using a gaseous diluent, in general it is recommended that the starting material(s) constitute from about 1 to about 95, and preferably about 5 to about 50, mole percent of the starting material/carrier feed. Increasing the dilution of the starting material with a gaseous diluent such as hydrogen may tend to increase the selectivity of the reaction to the particular products desired. The amount of liquid diluent can vary widely, for instance, from no diluent to about 90 weight percent or greater of the total weight of the starting materials.

For processes of this invention in which a nonaromatic carboxylated N,N,N-trisubstituted nitrogen-containing compound(s) is heated at an elevated temperature for a period of time sufficient to produce a nonaromatic N,N,N-trisubstituted nitrogen-containing compound or a nonaromatic N,N-disubstituted nitrogen-containing compound and a $CO_2$ synthon are heated at an elevated temperature for a period of time sufficient to produce a nonaromatic N,N,N-trisubstituted nitrogen-containing compound or other related processes described herein, it is understood that the process conditions described herein for the step (ii) decarboxylation reaction can desirably be employed for such processes.

The processes of this invention are useful for preparing nonaromatic N,N,N-trisubstituted nitrogen-containing compounds such as those embraced by the formulae $RN(R_1)R$ or $RN(R_2)R$ wherein R, $R_1$ and $R_2$ are as defined above. It is understood that the R substituents together can complete a heterocycloalkyl ring which can be substituted or unsubstituted. Illustrative nonaromatic N,N,N-trisubstituted nitrogen-containing compounds prepared by the processes of this invention include, for example, 1-methylpiperazine, 1,4-dimethylpiperazine, 1-ethylpiperazine, 1,4-diethylpiperazine, 1-(N-hydroxyethyl)ethylpiperazine, 1-methyl-4-aminoethylpiperazine, N-(1-piperazinoethyl)ethylenediamine, 1-aminoethylpiperazine, 1,4-diaminoethylpiperazine, 1-aminoethylmorpholine, 4-methylmorpholine, 4-ethylmorpholine and the like.

Illustrative of suitable nonaromatic N,N,N-trisubstituted nitrogen-containing compounds which can be prepared by the processes of this invention include those permissible nonaromatic N,N,N-trisubstituted nitrogen-containing compounds, including any permissible derivatives of described nonaromatic N,N,N-trisubstituted nitrogen-containing compounds, which are described in Kirk-Othmer, Encyclopedia of Chemical Technology, Third Edition, 1984, the pertinent portions of which are incorporated herein by reference.

The nonaromatic N,N,N-trisubstituted nitrogen-containing compound products produced by the processes of this invention can be separated by distillation. For example, a crude reaction product can be subjected to a distillation-separation at atmospheric or reduced pressure through a packed distillation column. Reactive distillation may be useful in conducting the step (i) transesterification reaction.

The processes of this invention may be carried out using, for example, a fixed bed reactor, a fluid bed reactor, or a slurry reactor. The optimum size and shape of the catalyst will depend on the type of reactor used. In general, for fluid bed reactors, a small, spherical catalyst particle is preferred for easy fluidization. With fixed bed reactors, larger catalyst particles are preferred so the back pressure within the reactor is kept reasonably low.

The processes of this invention can be conducted in a batch or continuous fashion, with recycle of unconsumed starting materials if required. The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials at an elevated temperature. When complete conversion is not desired or not obtainable, the starting materials can be separated from the nonaromatic N,N,N-trisubstituted nitrogen-containing compound product, for example by distillation, and the starting materials then recycled back into the reaction zone.

The processes are conducted for a period of time sufficient to produce the nonaromatic N,N,N-trisubstituted nitrogen-containing compound products. The exact reaction time employed is dependent, in part, upon factors such as temperature, nature and proportion of starting materials, and the like. The reaction time will normally be within the range of from about one-half to about 100 hours or more, and preferably from less than about one to about ten hours.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Illustrative of suitable reactants in effecting the processes of this invention include by way of example:
PIP - piperazine
UR - urea
OX - 2-oxazolidinone
MO - morpholine
EC - ethylene carbonate
PC - propylene carbonate
DMC - dimethyl carbonate
DEC - diethyl carbonate
DEA - diethanolamine
HEO - N-(2-hydroxyethyl) 2-oxazolidinone
AEO - N-(2-aminoethyl) 2-oxazolidinone
MEA - monoethanolamine
AEEA - aminoethylethanolamine
MP - 1-methylpiperazine
EP - 1-ethylpiperazine
HEP - 1-hydroxyethylpiperazine
AEP - 1-aminoethylpiperazine
MPC - methyl 1-piperazine carboxylate
EPC - ethyl 1-piperazine carboxylate
MMPC - methyl 4-methyl-1-piperazine carboxylate
EEPC - ethyl 4-ethyl-1-piperazine carboxylate
MMC - methyl 1-morpholine carboxylate
EMC - ethyl 1-morpholine carboxylate Illustrative of suitable products prepared by the processes of this invention include by way of example:
AEP - 1-aminoethylpiperazine
DAEP - 1,4-diaminoethylpiperazine
AEM - 1-aminoethylmorpholine
MM - 4-methylmorpholine
EM - 4-ethylmorpholine
DMP - 1,4-dimethylpiperazine
MP - 1-methylpiperazine
EP - 1-ethylpiperazine DEP - 1,4-diethylpiperazine
HEEP - 1-(N-hydroxyethyl)ethylpiperazine
MAEP - 1-methyl-4-aminoethylpiperazine
PEEDA - N-(1-piperazinoethyl)ethylenediamine Illustrative of permissible reactions encompassed within the scope of this invention include, for example, the following reactant/product combinations:

| REACTANT(S) | PRODUCT(S) |
|---|---|
| MO, DMC | MM |
| PIP, OX | AEP, DAEP |
| MO, OX | AEM |
| PIP, DMC | DMP, MP |
| MEA, EC, PIP | AEP |
| AEEA, EC, PIP | PEEDA |
| MP, DMC | DMP |
| PIP, HEO | HEEP |
| PIP, AEO | PEEDA |

As used herein, the phrase "residue of an organic compound" is contemplated to include all permissible residues of organic compounds. In a broad aspect, the permissible residues include acyclic and cyclic, branched and unbranched, carbocyclic and heterocyclic, aromatic and nonaromatic residues of organic compounds. Illustrative organic compound residues include, for example, alkyl, aryl, cycloalkyl, heterocycloalkyl, alkyl(oxyalkylene), aryl(oxyalkylene), cycloalkyl(oxyalkylene), heterocycloalkyl(oxyalkylene), hydroxyalkyl, hydroxyalkyl(oxyalkylene), hydroxy(alkyleneoxy) and the like. The permissible residues can be substituted or unsubstituted and the same or different for appropriate organic compounds. This invention is not intended to be limited in any manner by the permissible residues of organic compounds.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxy, hydroxyalkyl, amino, aminoalkyl, halogen and the like in which the number of carbons can range from 1 to about 20 or more, preferably from 1 to about 12. The permissible substituents can be one or more and the same or different for appropriate organic compounds. This invention is not intended to be limited in any manner by the permissible substituents of organic compounds.

The following examples are provided to further illustrate the processes of this invention.

EXAMPLES 1-7

The following procedure was used for the preparation of nonaromatic N,N,N-trisubstituted nitrogen-containing compounds in Examples 1-7. The reactions were conducted in a Parr mini-reactor equipped with a 300 milliliter autoclave, a heating mantle, and a variable speed motor-driven stirrer. The reaction temperature was monitored by a Doric Trendicator 400A and cooling was performed by introducing cold water through a cooling loop. An amount of piperazine or morpholine and 2-oxazolidinone indicated in Table I below was placed in the autoclave and the system was evacuated and purged with nitrogen through a three-way valve. A total of 15 psig of nitrogen was charged to the autoclave and the reactants heated to the indicated temperature in Table I for a period of time indicated in Table I. The autoclave was cooled to room temperature and the product mixture analyzed by capillary gas chromatography (FID) using a DB-1701 column. The results are set forth in Table I.

TABLE I

| | Example No. | | | | | | |
|---|---|---|---|---|---|---|---|
| | 1 | 2 | 3 | 4 | 5 | 6 | 7 |
| Process Parameters | | | | | | | |
| Piperazine, grams | 25.48 | 43.10 | 18.95 | 43.10 | 37.90 | 43.10 | — |
| Morpholine, grams | — | — | — | — | — | — | 31.36 |
| 2-Oxazolidinone, grams | 21.78 | 21.78 | 34.80 | 21.78 | 9.58 | 21.78 | 26.12 |
| Temperature, °C. | 200 | 200 | 200 | 150 | 200 | 150 | 200 |
| Duration of run, hours | 2 | 2 | 2 | 4 | 2 | 11 | 2 |
| Crude Product, grams | 38.0 | 59.6 | 38.7 | 63.9 | 44.8 | 60.6 | 51.1 |
| Product Composition area % | | | | | | | |
| Monoethanolamine | 4.74 | 3.28 | 11.14 | 2.45 | 1.09 | 3.87 | 3.47 |
| Piperizine | 56.22 | 65.52 | 26.96 | 79.31 | 89.42 | 77.17 | — |
| Morpholine | — | — | — | — | — | — | 40.89 |
| Aminoethylpiperazine | 27.48 | 25.42 | 28.42 | 6.57 | 6.69 | 12.07 | — |
| Aminoethylmorpholine | — | — | — | — | — | — | 36.33 |
| 2-Oxazolidinone | 1.36 | 2.75 | 3.97 | 11.04 | 2.45 | 3.59 | 6.41 |
| 1,4-Diaminoethylpiperazine | 5.81 | 1.12 | 16.63 | — | — | 1.26 | — |
| Hydroxyethylethyleneurea | 1.55 | 0.55 | 5.25 | 0.12 | — | 0.32 | 3.22 |
| Piperazinoethylethylenediamine urea | 2.35 | 0.87 | 4.71 | 0.22 | — | 0.63 | — |
| Morpholinoethylethylenediamine urea | — | — | — | — | — | — | 9.66 |
| Others | — | — | 2.12 | — | — | — | — |

EXAMPLE 8

Into a 50 milliliter 3-neck round bottom reaction flask equipped with a thermometer, mechanical stirrer and distillation head was added 4.31 grams (0.05 mol) of piperazine and 5.40 grams (0.06 mol) of dimethyl carbonate which were dissolved in 20 milliliters of toluene. The reaction mixture was heated at reflux overnight under a nitrogen atmosphere. At a head temperature of 64° C. and a kettle temperature of 95° C., the condensate was removed slowly overhead until the head temperature reached 86° C., at which point the reaction mixture was again allowed to reflux overnight. After cooling, the reaction mixture was analyzed by capillary gas chromatography (FID) using a DP-1701 column. The results are set forth in Table II below.

TABLE II

| Product Composition, area % | |
|---|---|
| Dimethyl carbonate | 10.50 |
| 1,4-Dimethylpiperazine | 8.58 |
| 1-Methylpiperazine | 38.74 |
| Piperazine | 29.12 |
| Methyl 4-methyl-1-piperazine carboxylate | 3.10 |
| Methyl 1-piperazine carboxylate | 8.88 |
| Bis(methyl 1-piperazine carboxylate) | 0.60 |

EXAMPLE 9

Into a 50 milliliter 3-neck round bottom reaction flask equipped with a thermometer, mechanical stirrer and distillation head was added 4.36 grams (0.05 mol) of morpholine and 5.40 grams (0.06 mol) of dimethyl carbonate which were dissolved in 20 milliliters of toluene. The reaction mixture was heated at reflux for a period of about 50 hours under a nitrogen atmosphere. The head temperature was 93° C. and the kettle temperature was 105° C. After cooling, the reaction mixture was analyzed by capillary gas chromatograph (FID) using a DB-1701 column. The results are set forth in Table III below.

TABLE III

| Product Composition, area % | |
| --- | --- |
| Dimethyl carbonate | 18.28 |
| N-Methylmorpholine | 8.68 |
| Morpholine | 59.87 |
| Methyl 1-morpholine carboxylate | 1.06 |

Although the invention has been illustrated by the preceding examples, it is not to be construed as being limited thereby; but rather, the invention encompasses the generic area as hereinbefore disclosed. Various modifications and embodiments can be made without departing from the spirit and scope thereof.

I claim:

1. A process for preparing nonaromatic cycle nitrogen-containing compounds which comprises heating a compound selected from the group consisting of methyl 1-piperazine carboxylate, ethyl 1-piperazine carboxylate, methyl 4-methyl-1-piperazine carboxylate, ethyl 4-ethyl-1-piperazine carboxylate, methyl 4-morpholine carboxylate and ethyl 4-morpholine carboxylate, at a temperature from about 50° C. to about 300° C., for a period of time from about 0.5 hours to about 100 hours, to produce the corresponding nonaromatic cyclic nitrogen-containing compound selected from the group consisting of 1-methylpiperazine, 1-ethylpiperazine, 1,4-dimethylpiperazine, 1,4-diethylpiperazine, 4-methylmorpholine and 4-ethyl morpholine, respectively.

2. The process of claim 1 wherein the temperature is from about 75° C. to about 250° C.

3. A process for preparing nonaromatic cyclic nitrogen-containing compounds which comprises (i) contacting a compound selected from the group consisting of piperazine, 1-methylpiperazine, 1-ethylpiperazine and morpholine, with a compound selected from the group consisting of dimethyl carbonate and diethyl carbonate, under conditions effective to produce the corresponding intermediate nonaromatic cyclic carboxylated nitrogen-containing compound selected from the group consisting of methyl-1-piperazine carboxylate, ethyl-1-piperazine carboxylate, methyl-4-methyl-1-piperazine carboxylate, ethyl 4-ethyl-1-piperazine carboxylate, methyl 4-morpholine carboxylate and ethyl 4-morpholine carboxylate, and (ii) subsequently heating the nonaromatic cyclic carboxylated nitrogen-containing compound, at a temperature from about 50° C. to about 300° C., and a time from about 0.5 hours to about 100 hours, to produce the corresponding nonaromatic cyclic nitrogen-containing compound selected from the group consisting of 1-methylpiperazine, 1-ethylpiperazine, 1,4-dimethylpiperazine, 1,4-diethylpiperazine, 4-methylmorpholine and 4-ethylmorpholine.

4. The process of claim 3 wherein the temperature is from about 75° C. to about 250° C.

5. A process for preparing nonatomic cyclic nitrogen-containing compounds which comprises contacting a nonaromatic cyclic nitrogen-containing compound selected from the group consisting of piperazine, 1l-methylpiperazine, 1-ethylpiperazine and morpholine, with a compound selected from the group consisting of dimethyl carbonate, diethyl carbonate and 2-oxazolidinone, at a temperature of from about 50° C. to about 300° C., and for a period of time from about 0.5 hours to about 100 hours to produce the corresponding nonaromatic cyclic nitrogen-containing compound selected from the group consisting of 1-methylpiperazine, 1-ethylpiperazine, 1,4-dimethylpiperazine, 1,4-diethylpiperazine, 1-methyl-4-aminoethylpiperazine, 1j-aminoethylpiperazine, 1,4-diaminoethylpiperazine, 4-aminoethylmorpholine, 4-methylmorpholine and 4-ethylmorpholine.

6. The process of claim 5 wherein 2-oxazolidinone is produced in situ by reacting ethylene carbonate and monoethanolamine.

7. The process of claim 5 wherein the temperature is from about 75° C. to about 250° C.

* * * * *

UNITED STATES PATENT AND TRADEMARK OFFICE
CERTIFICATE OF CORRECTION

PATENT NO. : 5,262,534
DATED     : November 16, 1993
INVENTOR(S) : Stephen W. King It is certified that error appears in the above-identified patent and that said Letters Patent is hereby corrected as shown below:

In column 11, line 23, the word "cycle" should read "cyclic".

In column 12, line 20, the word "nonatomic" should read "nonaromatic".

In column 12, line 23, the number "11-" should read "1-".

In column 12, line 33, the word "lj-aminoe-" should read "1-aminoe-".

Signed and Sealed this

Twenty-sixth Day of April, 1994

Attest:

BRUCE LEHMAN

*Attesting Officer*    *Commissioner of Patents and Trademarks*